(12) United States Patent
Funk

(10) Patent No.: US 8,314,840 B1
(45) Date of Patent: Nov. 20, 2012

(54) MOTION ANALYSIS USING SMART MODEL ANIMATIONS

(76) Inventor: Conley Jack Funk, Fort Myers, FL (US)

( * ) Notice: Subject to any disclaimer, the term of this patent is extended or adjusted under 35 U.S.C. 154(b) by 0 days.

(21) Appl. No.: 13/229,689

(22) Filed: Sep. 10, 2011

(51) Int. Cl.
*H04N 7/18* (2006.01)
(52) U.S. Cl. .................. 348/157; 434/247; 434/252
(58) Field of Classification Search .......... 348/157; 382/103, 107; 434/247, 252, 262; 473/222; 482/8
See application file for complete search history.

(56) References Cited

U.S. PATENT DOCUMENTS

| | | | |
|---|---|---|---|
| 5,772,522 A * | 6/1998 | Nesbit et al. ............ | 473/222 |
| 5,904,484 A * | 5/1999 | Burns ..................... | 434/252 |
| 6,293,802 B1 * | 9/2001 | Ahlgren .................. | 434/252 |
| 6,514,081 B1 * | 2/2003 | Mengoli .................. | 434/252 |
| 6,567,536 B2 * | 5/2003 | McNitt et al. ........... | 382/107 |
| 7,766,794 B2 * | 8/2010 | Oliver et al. ............ | 482/8 |
| 8,021,160 B2 * | 9/2011 | Chang .................... | 434/262 |
| 2005/0196737 A1 * | 9/2005 | Mann ..................... | 434/247 |
| 2009/0220124 A1 * | 9/2009 | Siegel .................... | 382/103 |

* cited by examiner

*Primary Examiner* — Sath V Perungavoor
*Assistant Examiner* — James Pontius

(57) ABSTRACT

The invention relates to a method and a system for analyzing, teaching and identifying the biomechanics of body motion from a video source. Repeatable body motion activities are analyzed as a series of positions of interest that trigger superimposed smart model animations. The properties of body part images, including location, scale and rotation are determined by a combination of manual and automatic means thereby tailoring the smart models to the underlying video images of the body in motion. Based on the proximity of the subject's actual motion to the ideal-or-expected motion defined for the smart models, quantitative characterizations of the motion performance are made.

17 Claims, 11 Drawing Sheets

MOTION ANALYSIS USING SMART MODEL ANIMATIONS

CROSS REFERENCE OF RELATED APPLICATIONS (none)

STATEMENT REGARDING FED SPONSORED R & D (none)

REFERENCE TO MICROFICHE APPENDIX (none)

FIELD OF THE INVENTION

The invention relates to a system for analyzing, teaching and identifying body motion from a video source by recognizing asynchronous positions-of-interest that trigger smart model animations.

BACKGROUND AND DESCRIPTION OF PRIOR ART

Many different techniques, over the course of time have been used to teach or understand the mechanics of various repeatable human motions, including sports motion. Many trainers use a video analysis system to teach a subject how to perform basic motion, especially with club, bat and racket sports. The trainer records and replays the recorded video information to illustrate the subject's performance while providing feedback.

Feedback often takes the form of verbal remarks or drawings made by the instructor relative to problems of posture or technique followed by suggestions on correcting the problems. Visualizing one's personal performance has been recognized as a valuable tool in identifying problems and correcting problems in order to improve motion techniques. Although video analysis systems are widely used, these systems have the obvious limitation that a knowledgeable trainer is required to analyze the video information. This kind of analysis is often subjective or inaccurate and may be expensive.

Often, these video analysis systems are capable of comparing the subject's recorded motion with a similar motion performed by a qualified professional that is superimposed over the same recording. U.S. Pat. No. 6,514,081 Mengoli allows the subject to analyze differences between his or her motion and the master's motion with emphasis on synchronization of motion.

Several video analysis systems teach methods where analysis is strictly related to synchronization of multiple information signals. This can severely restrict the kinds of motion activities available to the subject and the apparatus for analysis.

The relative slowness of the thinking speed of the subject compared to the muscle memory speed of the master makes it unclear how the techniques of one human are optimal for another given different bodies, especially different brains and muscles. It has been estimated that as many as 100 different muscles are required to be coordinated during the performance of some sports activities.

The extent to which the body parts and posture and consequently the motion performance of the subject and any chosen professional could or should match to represent a relevant and excellent or fitting performance model for the subject are sometimes questionable. Prior art includes systems that place inertial sensors on the body of the subject, reflecting tapes on the subject's body and if applicable on his bat, racquet or club. In U.S. Pat. No. 7,264,554 Bentley teaches a system and method that instruments the subject with inertial sensors attached to a vest and glove. When the subject is outfitted beyond the minimum requirements to perform the motion, the expense, possibly the skewed nature of the performance and other limitations are brought into question.

In the field of identification of biometric motion, in U.S. Pat. No. 7,844,081 McMakin employs imaging systems and methods to generate a motion signature. The analysis is shown to be inaccurate due to clothing. The use of techniques that get around clothing can be invasive.

All of the commercially available systems lack the total set of features necessary to significantly impact the field of biomechanics for analysis, teaching and identification. All methods taught in prior art suffer from one or more disadvantages. Some are impractical in their use. Some are sufficiently clumsy or cumbersome to skew the results. Some require unnatural settings. Many are imprecise in their measurements or imprecise or ineffective in their presentations. Some focus on one or more masters that may not be the best models. Some are too restrictive by requiring synchronizations of multiple information sources. All seem to lack the ability to be adjusted properly to match the subject.

What is lacking in the field is a simple, accurate and affordable motion analysis system which is capable of precisely demonstrating effective solutions for a variety of motion problems.

It is with respect to these and other considerations that the present invention has been made.

SUMMARY OF THE INVENTION

In view of the foregoing background, it is therefore an object of the invention to provide a system for analyzing and teaching biometric performance that is practical and affordable.

It is further an object of the invention to provide effective analysis and presentation for asynchronous positions-of-interest based solely on the extemporaneous actions of the subject and not upon timing or synchronization of sources of information.

It is further an object of the invention that during the performance of the analyzed motion, the subject is not distracted or encumbered by requirements to wear or hold equipment, sensors or reflectors beyond that which is minimally required to perform the motion.

It is further an object of the invention that during the performance of the analyzed motion, the subject is not required to perform in a setting that is unnatural to the motion performance such as in front of a green screen background.

It is further an object of the invention to dynamically create smart models whose actual motion animations can verifiably reproduce the subject's motion with precisely the subject's body part measurements and location.

It is further an object of the invention to dynamically create smart models whose ideal-or-expected motion animation can represent ideal-or-expected performance. These smart models, while precisely matching the size of the body parts subject, are further adjustable according to externally provided specifications to represent a perfect model for performance.

It is further an object of the invention to dynamically create smart models with functional body parts that are easily adjustable by finger motion on a touch-screen or by a computer mouse in order to match the corresponding body parts in the video frames or to match position-of-interest properties such as expected-or-ideal motion properties.

It is further an objective that an adjustment of one body part of a smart model results in the appropriate adjustment of the others that are connected. For example, moving the hips sideways should adjust the torso and both legs concurrently. Similarly, bending a knee should rotate both the thigh and lower leg simultaneously in opposite directions.

It is further an object of the invention to dynamically create smart models that perform correction-of-position animations that can systematically animate the body part movements necessary to resolve discrepancies between the actual motion and the ideal-or-expected motion at selected positions-of-interest and thereby represent a solution that is specific, unmistakable and rich in instructional content for the subject.

It is further an object of the invention to perform smooth and continuous animations that illustrate the subtleties and interactions of all of the body parts.

It is further an object of the invention that the dynamically created smart models are able to be easily specified or modified by a subject or by an instructor to match external specifications, special requirements or physical limitations of the subject.

It is further an object of the invention to provide cooperative automatic and manually controlled capabilities to recognize body part images in video frames as a basis for the definition and adjustment of smart model transforms and properties.

It is further an object of the invention that the automatic approach uses a specialized video camera whereby each video frame contains skeletal coordinates. It is further an object of the invention that the automatic approach uses image-recognition processing to define and adjust the smart model animations.

It is further an object of the invention that the dynamically created smart models are adaptable to a wide range of motion activities.

These and other important advantages are inherent in the current invention.

In a preferred embodiment of the current invention, the system for analyzing a body in motion can be a practical and affordable hand-held phone camera. The system used for analysis could be as simple as smart phone. The current invention permits easy relocation of the smart model graphic of the body and its body parts in motion at any phase of the performance. This compensates for a jumpy or shifting body image that hand-held photography often produces.

A motion activity comprises one or more positions-of-interest that are generally characterized by specific pre-defined properties for specific body parts.

In just a few seconds, the subject can locate the starting position-of-interest and manually manipulate the superimposed smart model graphic to exactly match the body parts in the selected video frame. The prescribed process of manually manipulating a color-coded, superimposed smart model graphic to match the underlying video image by mouse movements or finger movements on a touch-sensitive screen is quick, exact and progressively educational. This precise matching of the subject's body parts and posture along with adjustments made according to externally supplied specifications about the nature of the ideal-or-expected motion allows the system to produce and display an ideal-or-expected motion animation that is a perfectly matched and excellent model for the subject's ideal-or-expected performance.

The current invention assists the subject in locating predetermined positions-of-interest as a function of body part, club, bat or racquet image properties. Once the positions-of-interest are determined, the smart model can perform the ideal-or-expected-motion animation as a sequence of animations, each triggered by realizing positions-of-interest in the sequential video frames displayed in the background.

Further, the subject can simultaneously advance the video and the smart model graphic to the various positions-of-interest, observing both the motion comparisons to get to a position-of-interest and the comparisons at that video position between the smart model graphic and the underlying body parts.

According to the subject's continued interest in the particular video, the subject can manually manipulate the superimposed smart model graphic at any or all of the positions-of-interest to match the underlying body part images in the video. This manual manipulation informs the smart model graphic of the transforms it needs to know to perform an actual-motion animation and allows the system to display comparisons of combinations of the ideal-or-expected-motion animation, the actual-motion animation and a correction-of-position motion animations over the sequential video frames.

The previously described manual manipulations further inform the smart model graphic of the subject's divergence from the ideal-or-expected performance. This allows the smart model graphic to perform the correction-of-position animations for each position-of-interest. The subject is able to see precisely and systematically how the actual motion of each of his or her body parts must change to achieve the ideal-or-expected motion as demonstrated by the smart model graphic with color coding which changes as body parts move into or out of conformance with ideal-or-expected properties.

The position-of-interest transform designator, who is possibly the subject or the instructor, can use the invention to create the ideal-or-expected animations to analyze many specific types of motion based on specific body motion templates that are included as a part of the current invention. The designer can locate and analyze an unlimited number of videos of relevant master performers publicly available on the internet using the current invention. Each analysis consumes only a couple of minutes and can generate copious data regarding the ideal location, the scale and the rotation of the body parts.

At the time the ideal-or-expected animation is displayed for the subject, the various transforms result in an animation that precisely matches the subject's body but is imbued with perfect performance characteristics.

The current invention provides the animations and comparisons uniformly for any type of biomechanical motion at all phases of the animation. Each smart model representation begins with a body-model template that is matched to the subject's body part image properties to form the body-model basis. This set of body-model basis properties are further transformed to the various position-of-interest properties.

Position-of-interest animations display the smart model smoothly and continuously between positions-of-interest and throughout the entire motion.

Repeatable motion activities such as calisthenics, weight-lifting, some kinds of gymnastics, yoga, Pilates, dancing in place, and sports that involve clubs, bats or racquets are relatively easy to analyze since the overall location of the body in motion is either stationary or very predictably nearby.

The video process for activities such as running and walking can be simplified by filming the subject on a treadmill.

Other repeatable motion activities where the subject must change his location are still possible due to the flexibility inherent in the current invention for easily manipulating the location coordinates, scale and rotation of the smart models.

Further included in the preferred embodiment is the accommodation of a live video source that contains the body part coordinates for each video frame. The current invention uses these body part coordinates in conjunction with the position-of-interest properties to automatically identify each position-of-interest and to produce and trigger the position-of-interest animations.

The live video recording is subsequently available to the subject as a fully-processed pre-recorded video, and the smart model graphics can be manually adjusted at any selected position-of-interest. All of the animations are available to the subject for review.

This live video source is very powerful, accurate, easy to use, commercially available and reasonably inexpensive. It attaches directly to a computer or a game console.

Further included in the preferred embodiment is the provision for a simple live video source, such as a webcam or camcorder. Image recognition processing present can supply some or all of the body part coordinates for the superimposed smart model graphics of the actual-motion animation. The image recognition processing can further identify some or all of the positions-of-interest from these coordinates.

The asynchronous, event driven framework of the current invention is most valuable for real-time analysis using live video sources. The subject can move his or her body freely at his or her own pace while the smart model animation generally tracks the subject, displaying the ideal-or-expected model superimposed over the subject's live video image.

The smart model position-of-interest animation is triggered by a starting cue from a position-of-interest whenever the subject's body part images are determined to be moving past the last matched position-of-interest. The smart model becomes a leading guide for the subject when he or she merely slows the pace of the motion between positions-of-interest.

Further, the subject can retrace his or her movements causing the position-of-interest animation to stop and then pick up again when the body image properties of the subject are matched to another position-of-interest. This feature provides unlimited repetition in order to perfect a given segment of the motion activity.

The current invention provides for audio responses that can be triggered at each selected position-of-interest thereby enriching the interactive process.

The current invention can be used to analyze the motion and techniques of a wide range of repeatable biomechanical activities including walking, running, dancing, exercise, relaxation techniques, martial arts, and sports activities including those using clubs, racquets or bats.

DETAILED DESCRIPTION OF THE PREFERRED EMBODIMENTS OF THE INVENTION

The following motion activity was chosen for detailed description due to its popularity as a much studied activity with repeatable motion. Accordingly, the current invention is not to be construed as limited to specific examples described herein but rather includes within its scope all embodiments allowed according to the appended claims.

Figure 1:
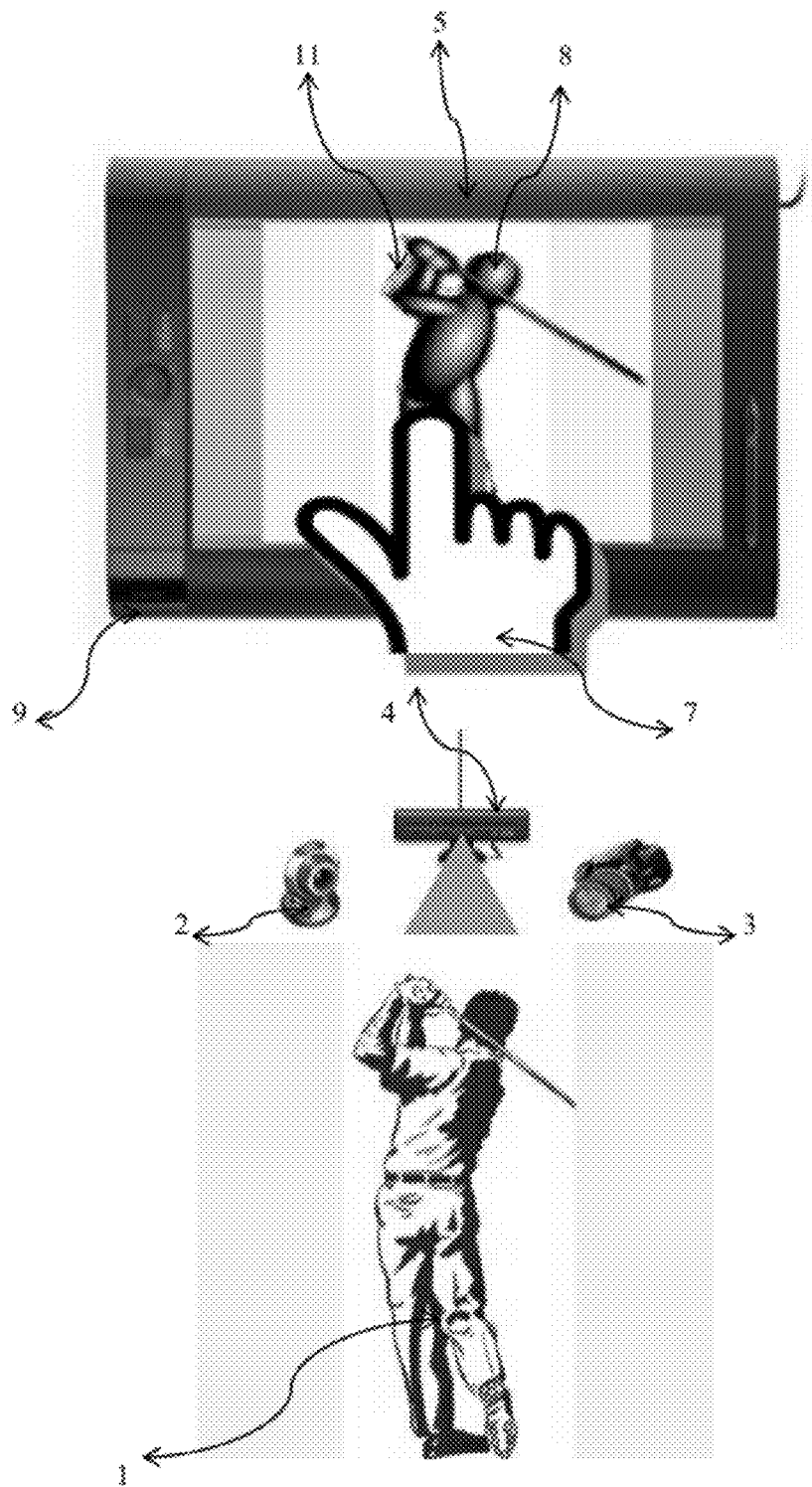
FIG. 1 shows a computer-based system configured for analyzing a body in motion from a video source. It further shows the act of capturing the video stream of body in motion, determining the body part images and superimposing a tailored body-model graphic directly over the body in motion in real-time on the computer display that represents the pre-defined ideal-or-expected motion.

A motion analysis system in accordance with the preferred embodiment of the current invention is shown in FIG. 1. Three different types of video cameras are shown recording a body in motion 1 in FIG. 1: a simple webcam 2 in FIG. 1; a digital camcorder 3 in FIG. 1; and an intelligent video camera 4 in FIG. 1. Each is supported by the current invention as a single alternative video source. The choice of video camera type is based on availability and other circumstances that may be dictated by the kind of motion activity being analyzed.

Figure 2:
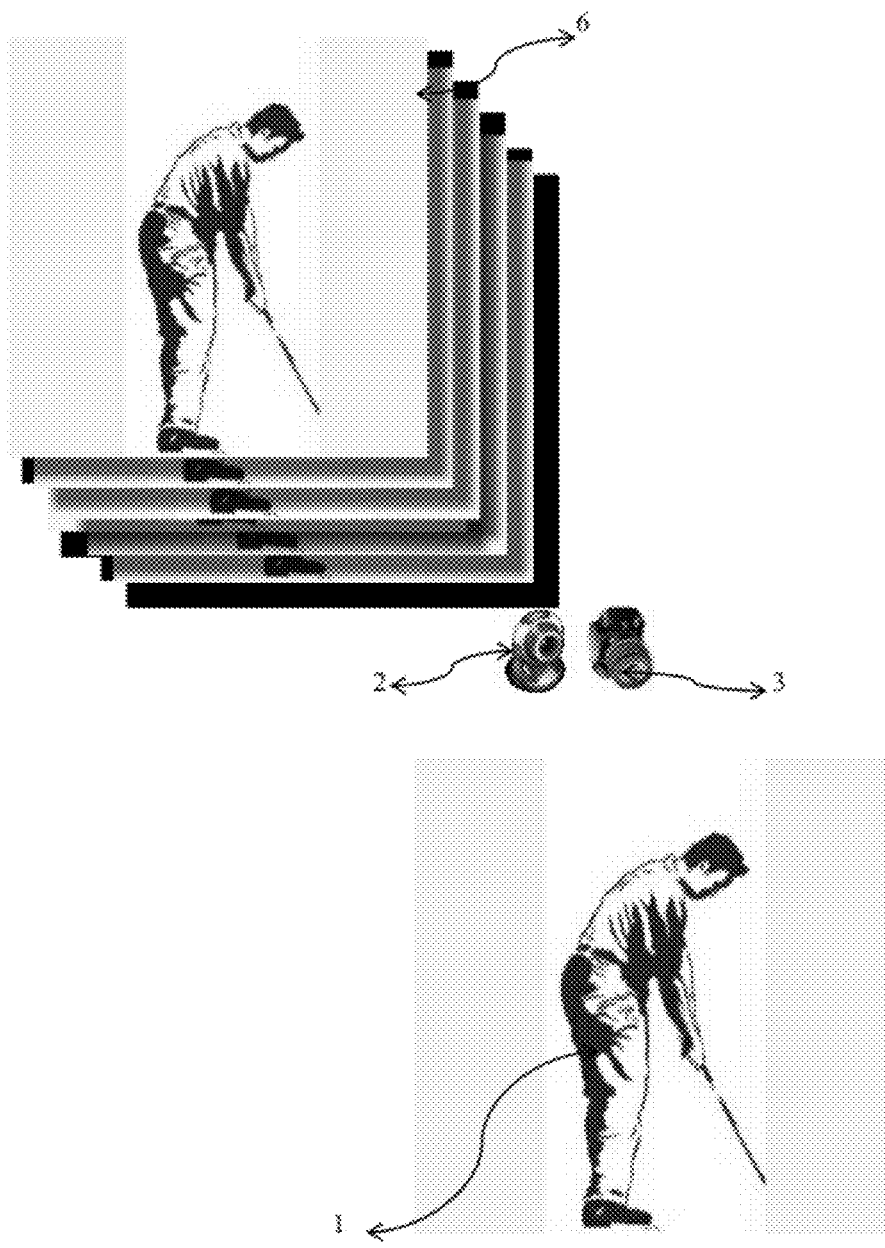
FIG. 2 shows the sequential video frames captured by simple cameras.
Figure 3:
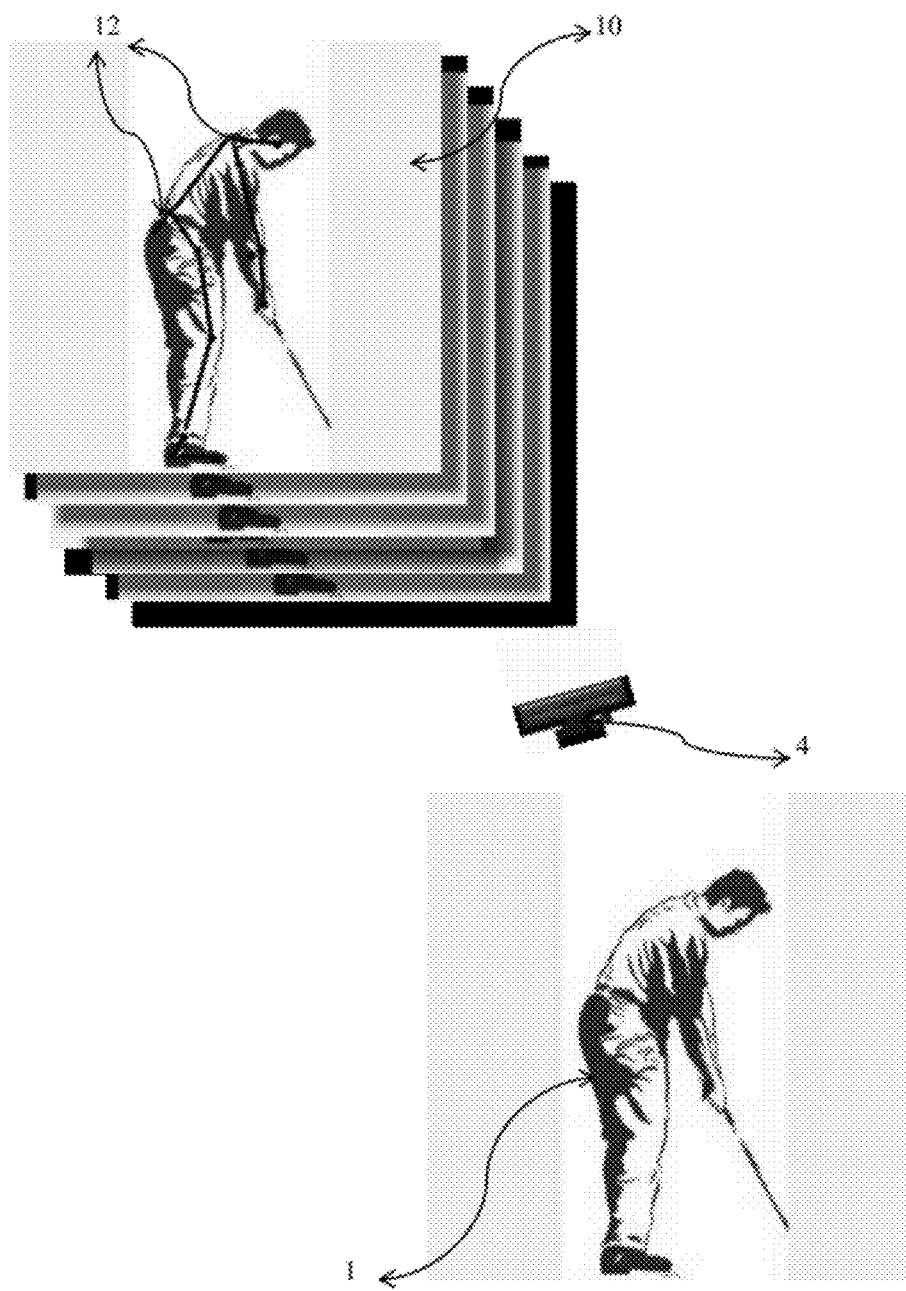
FIG. 3 shows the sequential video frames captured by an intelligent video camera that integrates skeletal video coordinates with each frame.

The CPU-Display-Speaker unit 5 in FIG. 1 receives sequential video frames 6 in FIG. 2 from a simple webcam 2 in FIG. 2 or from a video camcorder 3 in FIG. 2. The CPU-Display-Speaker unit 5 in FIG. 1 receives sequential video frames 10 in FIG. 3 from an intelligent video camera 4 in FIG. 3 that includes the skeletal coordinates 12 in FIG. 3 as an integral part of each frame.

Three techniques, heretofore called the collective techniques 7 in FIG. 1 for determining body part image properties are available. These techniques can be used in combination.

Figure 4:
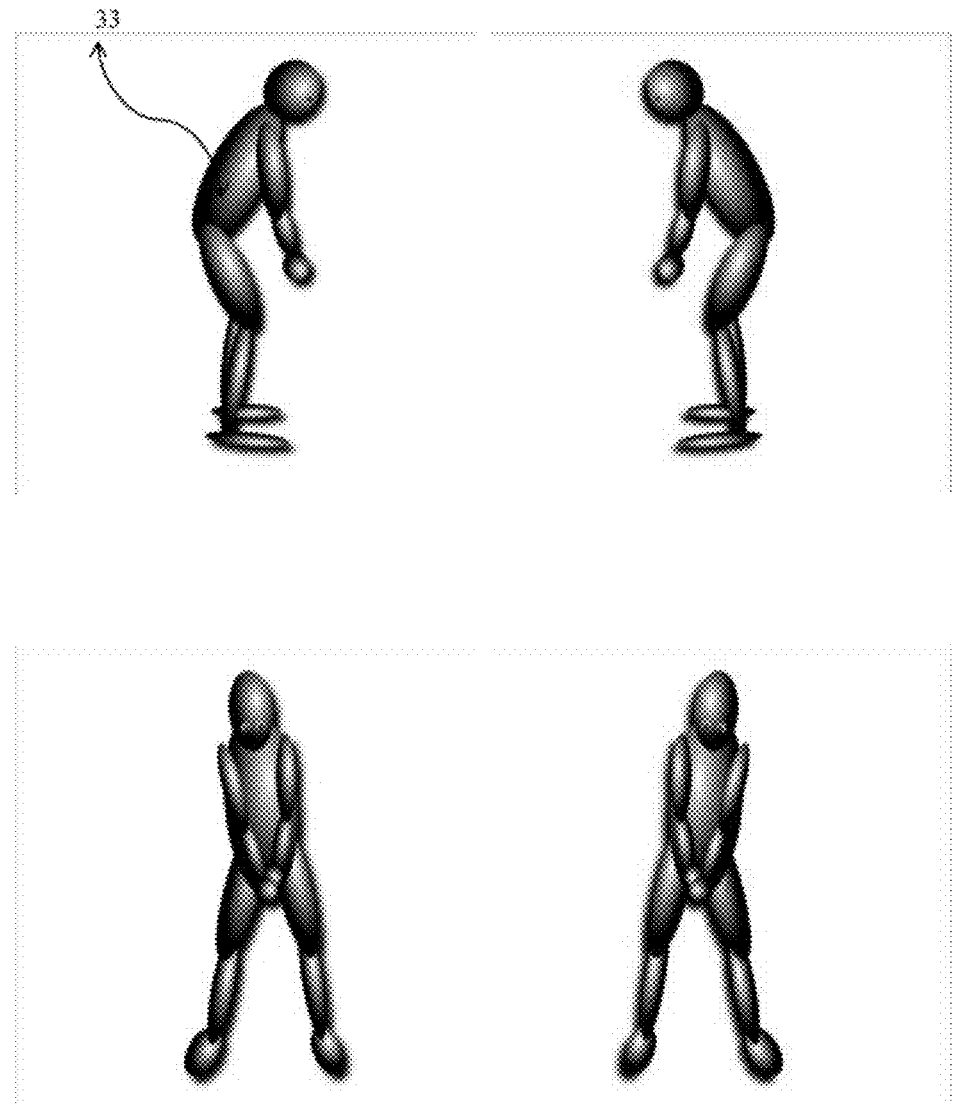
FIG. 4 shows a sample of body-model templates that correspond to specific motion activities that are manipulated to match the basis body parts images.

The first of the collective techniques 7 in FIG. 1 for determining body part image properties is by manual manipulation of the body parts of a superimposed graphic body-model 8 in FIG. 1 that begins with a body-model template 33 in FIG. 4 in this example. The final placement of the body part graphics determine the properties of the underlying body part images 11 in FIG. 1 relative to the body-model template 33 in FIG. 4, namely location, rotation and scale. The manual manipulation of the body part graphics is normally accomplished by finger motions on a touch sensitive display screen or by dragging motions using a computer mouse.

The second of the collective techniques 7 in FIG. 1 for determining body part image properties is by manipulation of the body parts of a superimposed graphic body-model 8 in FIG. 1 that begins with a body-model template 33 in FIG. 4, in this example. The CPU-Display-Speaker unit 5 in FIG. 1 receives sequential video frames 6 in FIG. 2 from a simple webcam 2 in in FIG. 2 or video camcorder 3 in FIG. 2. The body part image properties are based upon commercially available image recognition processing that yields the properties, namely location, scale and rotation as simple calculations.

The third of the collective techniques 7 in FIG. 1 for determining body part image properties is by manipulation of the body parts of a superimposed graphic body-model 8 in FIG. 1 that begins with a body-model template 33 in FIG. 4 in this example. The CPU-Display-Speaker unit 5 in FIG. 1 receives sequential video frames 10 in FIG. 3 from an intelligent video camera 4 in FIG. 3 that includes the skeletal coordinates 12 in FIG. 3 as an integral part of each sequential video frame 10 in FIG. 3 thereby yielding the properties of body part images such as location, scale and rotation as simple calculations.

Figure 5:
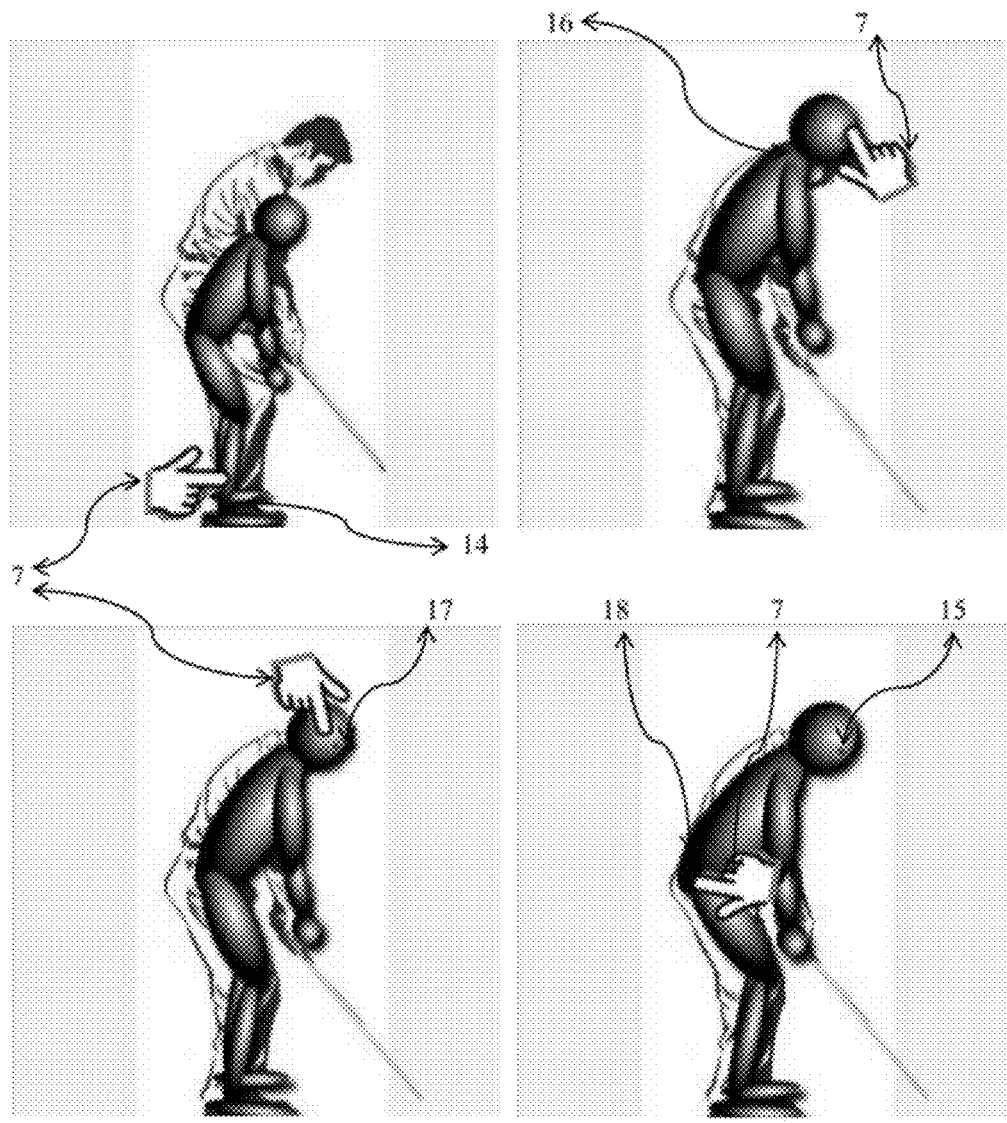
FIG. 5 shows the manipulation steps for determining body part image properties thereby transforming the template body-model properties of location, scale and rotation into the body part properties of basis body-model.

Any combination of collective techniques 7 in FIG. 1, can be used to modify a body-model template as shown in FIG. 4 and further to determine the properties of body parts including the body part properties of the basis body-model 15 shown in FIG. 5.

The determination of location properties 14 in FIG. 5 includes the determination of the XY coordinates of the body-model graphic as a whole and also the determination of XY coordinates of the body parts relative to the body-model template 33 in FIG. 4. In this example, the right foot 14 in FIG. 5 was predetermined to be the location basis for the body-model graphic.

The collective techniques 7 in FIG. 1 for determining body part image properties can be used to determine the scale of the body-model graphic 16 in FIG. 5. The determination of the properties of scale 16 includes the determination of the scale of the body-model graphic as a whole and also the determination of scale of the body parts relative to the body-model template 33 in FIG. 4. In this example, the body-model graphic is scaled upward 16 in FIG. 5 from the scale of the body-model template 33 in FIG. 4 to agree with the height of the underlying body-model image.

The collective techniques 7 in FIG. 1 for determining body part image properties can be used to determine the rotation of the body-model graphic 17 in FIG. 5. The determination of the properties of rotation 17 in FIG. 5 includes the determination of the rotation of the body-model graphic as a whole and also the determination of rotation of the body parts relative to the body-model template 33 in FIG. 4. In this example, the upper body of the body-model graphic is rotated forward 16 in FIG. 5 from the rotation of the upper body of the body-model template 33 in FIG. 4 to agree with forward waist-bend of the underlying body-model image.

The collective techniques 7 in FIG. 1 for determining body part image properties causes all connected body parts 18 in FIG. 5 such as torso and legs, to be changed whenever the properties of any one body part is changed. In this example, the pelvis area of the body-model graphic is pushed back 18 in FIG. 5 thereby rotating the torso and legs of the body-model graphic to further agree with forward waist-bend of the underlying body-model image.

Figure 8:
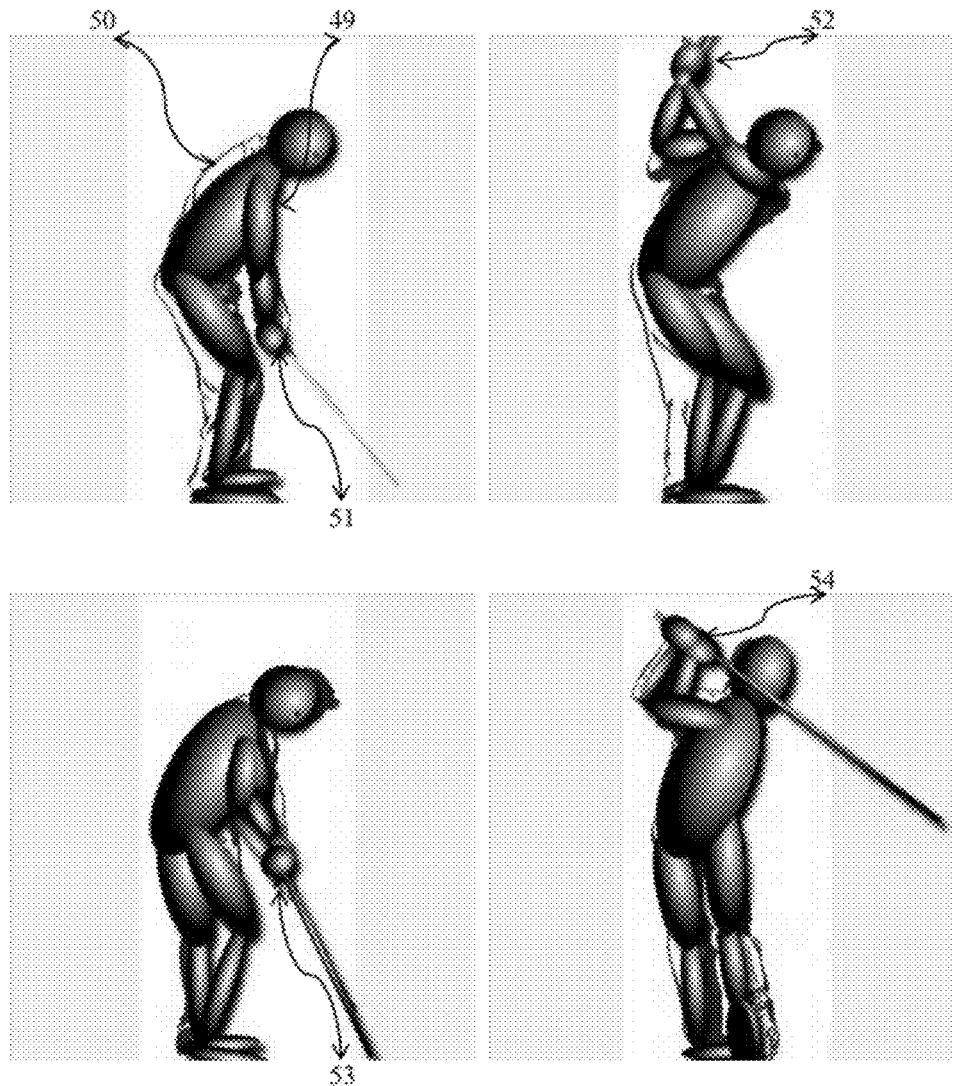
FIG. 8 shows the matching of body part images with the predefined ideal-or-expected body-model positions-of-interest.

FIG. 8 shows the matching of position-of-interest body part properties 49 in FIG. 8 with body part image properties 50 in FIG. 8. For this example, a first-fit technique for the properties of the hand body part images 51, 52, 53, 54 in FIG. 8 was used to establish the position-of-interest matches.

Figure 7:
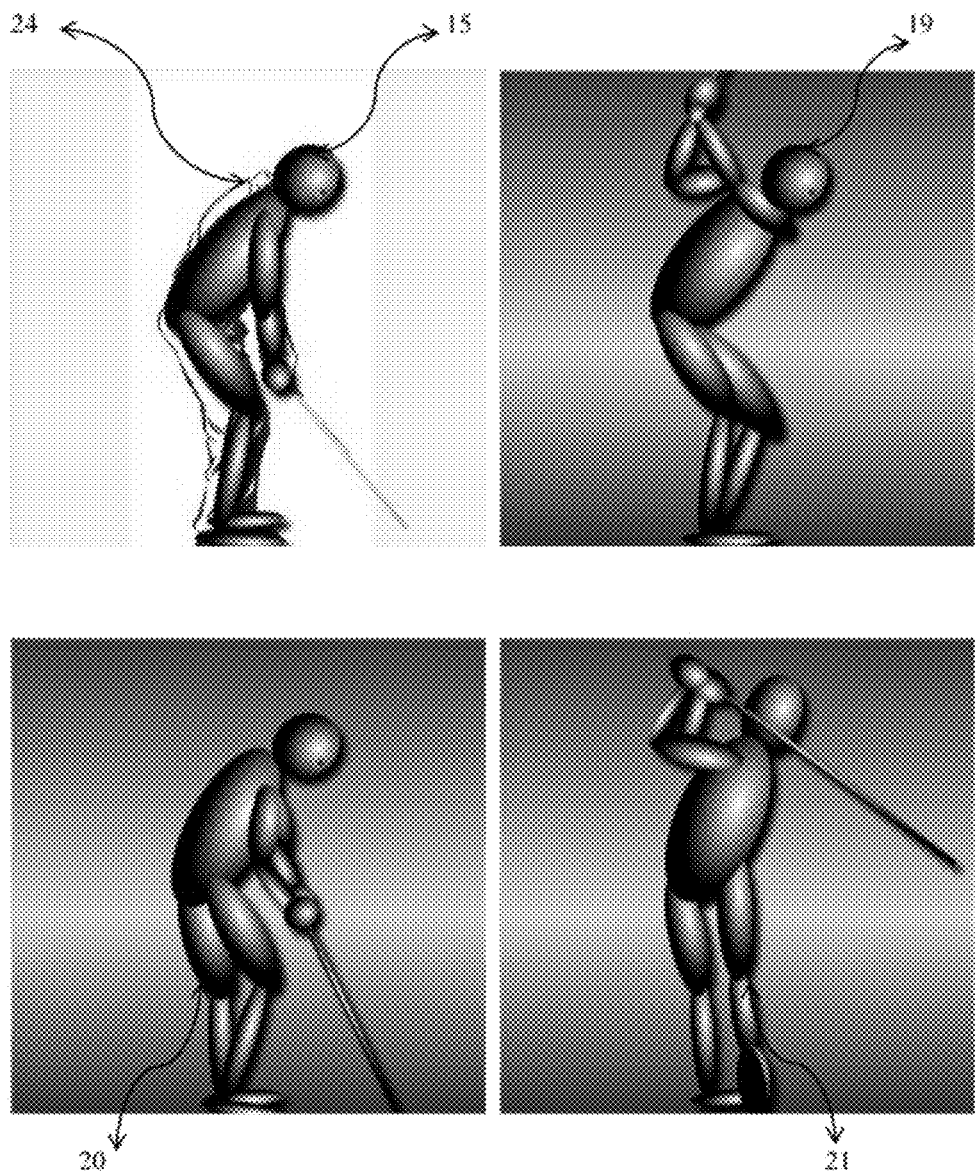
FIG. 7 shows the body-model graphics for positions-of-interest of a predefined ideal-or-expected body-model animation.

The body-model animation comprises four body-model positions-of-interest 15, 19, 20, 21 in FIG. 7. The first position-of-interest 15 in FIG. 7 is the body-model basis graphic that is derived from a body-model template 33 in FIG. 4 that can be predefined according to: a known standard; an external specification; an instructor; an investigator; a therapist; a researcher; or a subject. The transformations are similarly predefined that are applied to the properties of body parts to yield the positions-of-interest.

The body-model basis graphic 15 in FIG. 7 begins with a body-model template 33 in FIG. 4 that is transformed by one of the collective techniques 7 in FIG. 1 to determine the properties of the underlying body part images 24 in FIG. 7, thereby guaranteeing that the models are of the same scale as the underlying body part images throughout the animation as shown in FIG. 8.

The predefined position-of-interest body part transforms are applied to the properties of the basis body-model as a whole and its individual body parts 15 in FIG. 7 to yield the properties of the other positions-of-interest 19, 20, 21 in FIG. 7. The transforms include a location transform that yields the location property 14 in FIG. 5, a scale transform that yields a scale property 16 in FIG. 5 and a rotation transform that yields a rotation property 17 in FIG. 5. Additional body part rotation transforms determine the final properties of the body-model graphic 15 in FIG. 5.

The body-model animation of the complete motion activity in FIG. 7 further includes three position-of-interest animations that transform the body parts of the body-model smoothly and continuously from one position-of-interest to the next. These are position-of-interest animations resulting from the transformations of properties of the body-model graphic from 15 to 19, 19 to 20 and 20 to 21 in FIG. 7.

Figure 6:
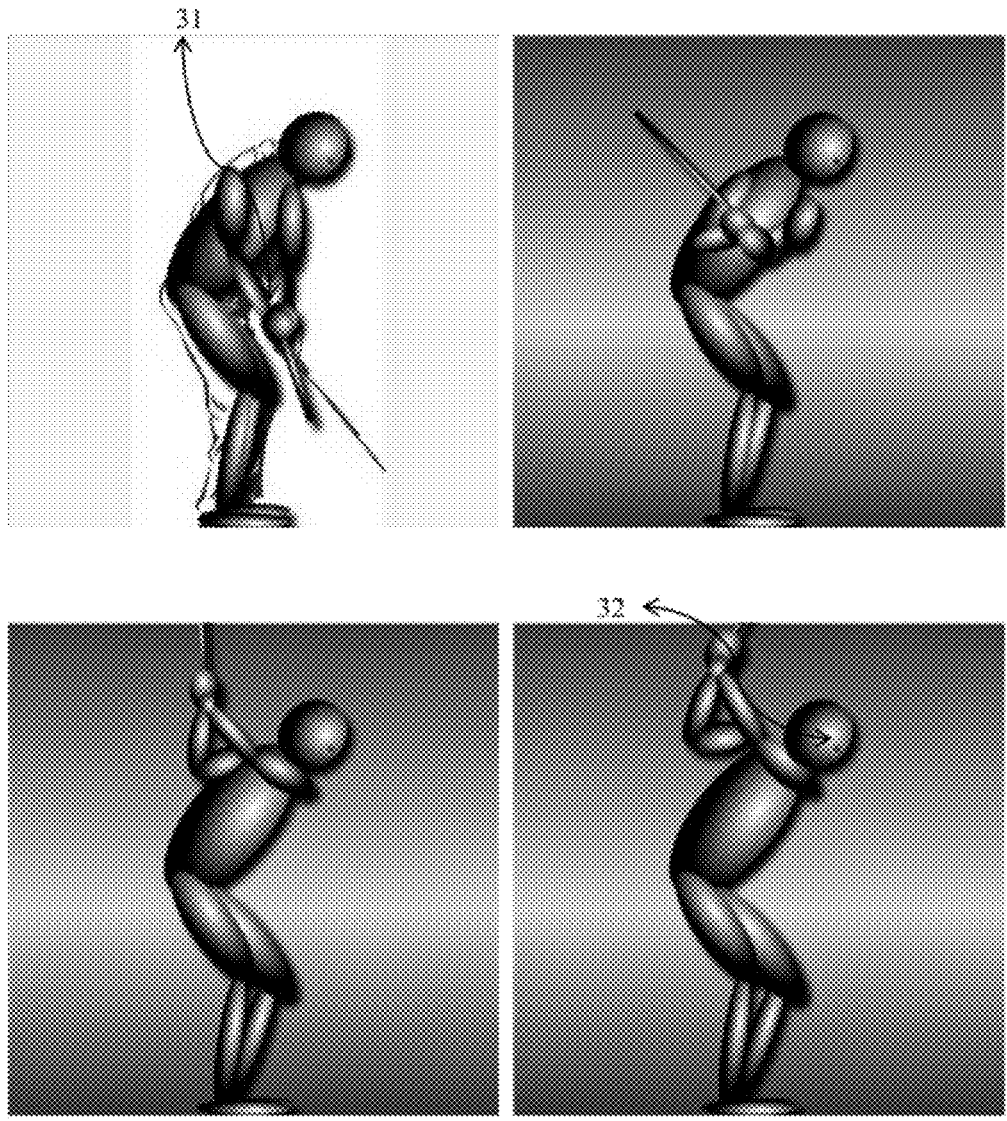
FIG. 6 shows a position-of-interest animation from one position-of-interest to the next position-of-interest initiated by a starting cue.

The position-of-interest animation of just one position-of-interest to the next shown in FIG. 6, demonstrates the transformation of 15 to 19 in FIG. 7. The position-of-interest animation shown in FIG. 6 transforms the body part properties of the basis body-model position-of-interest 15 in FIG. 5 to the body part properties of the next position-of-interest 32 in FIG. 6 over the course of "duration-of-animation" number of frames, which are four sequential video frames in this example. The animation is triggered by a starting cue 31 in FIG. 6 which is a recognition of motion away from the last matched body-model properties.

The position-of-interest animations remain still at one of the four matched positions-of-interest shown in FIG. 8 until a starting cue representing the subject's continued motion is recognized. This allows the subject to hesitate at positions-of-interest to receive analysis responses including audio feedback 9 shown in FIG. 1.

Figure 9:
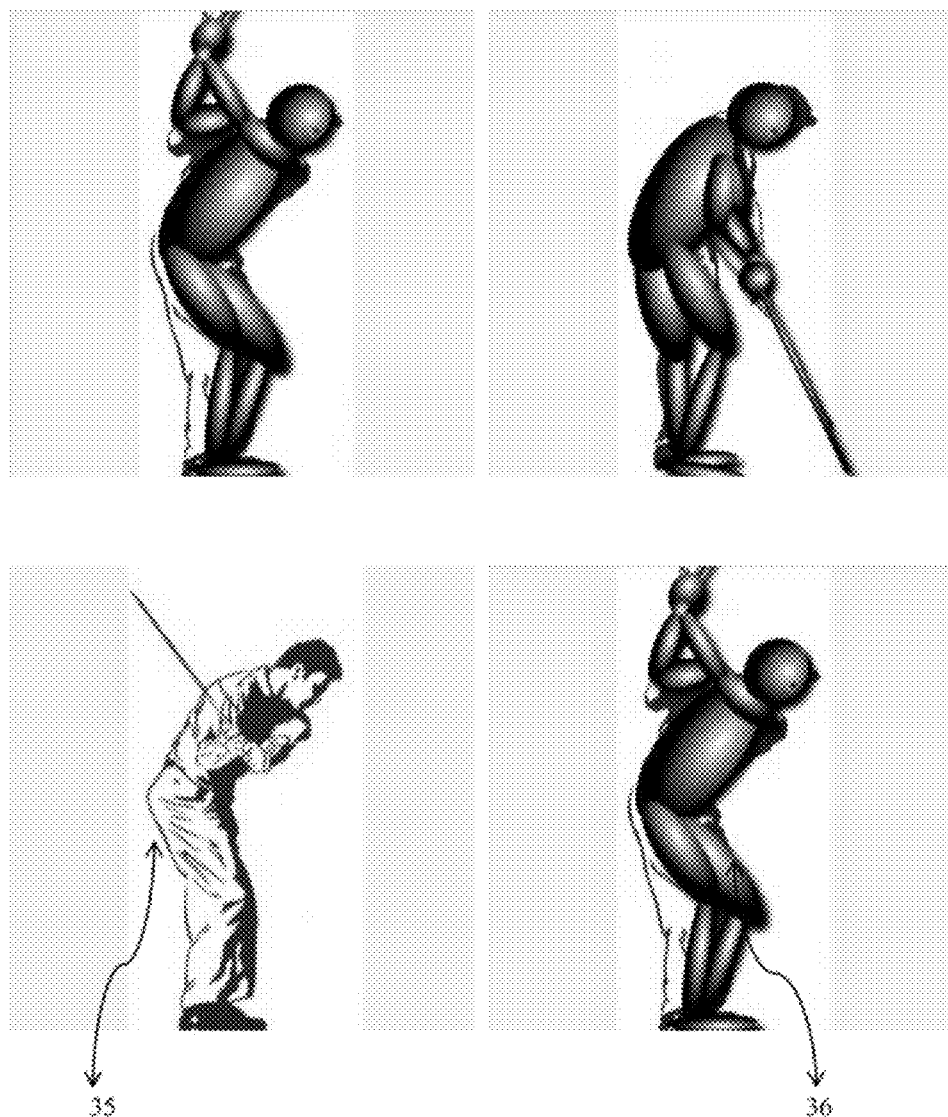
FIG. 9 shows an example of a real-time predefined ideal-or-expected body-model animation wherein the body in motion retraces his motion before completing the motion thereby causing the animation to stop and then to continue when the body part images of a previous or following position-of-interest are determined.

If the subject retraces his or her motion 35 in FIG. 9, the animation stops until a new position-of-interest is matched. In this example, the animation picks up again at 36 in FIG. 9.

Figure 10:
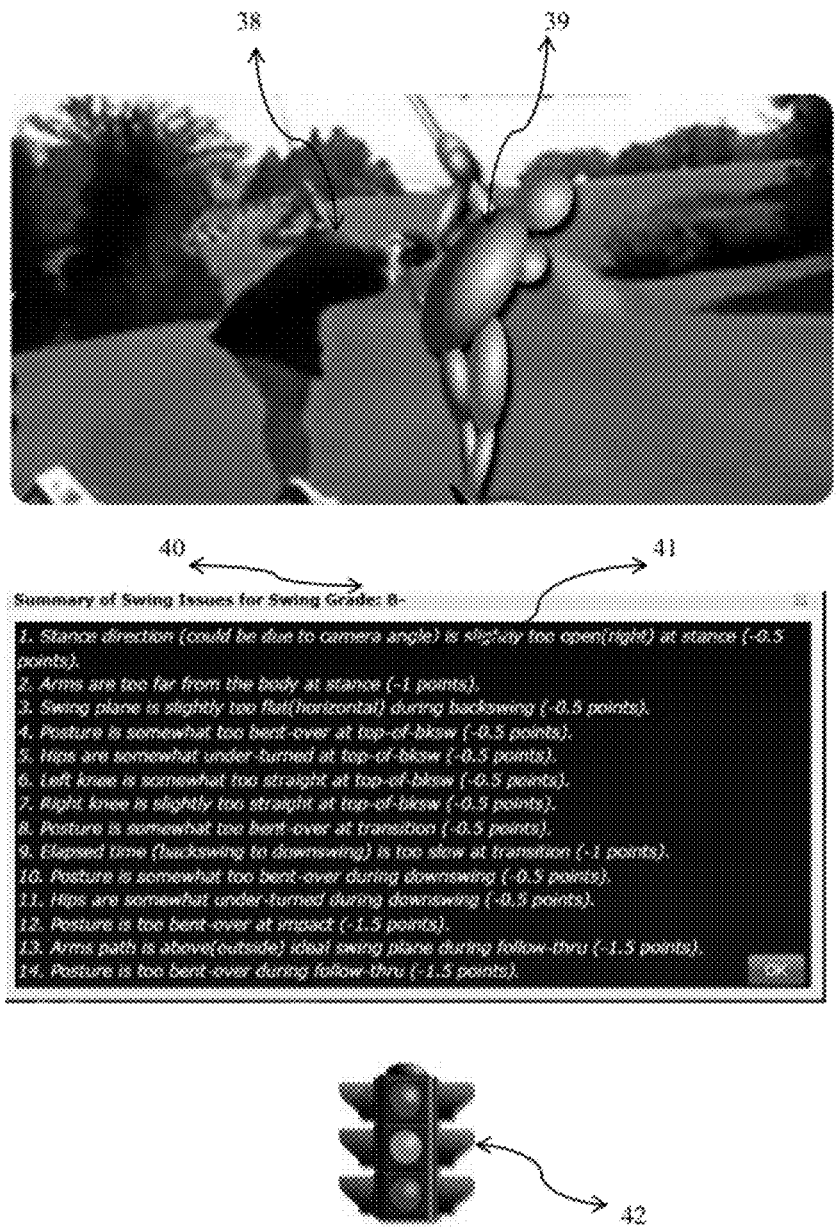
FIG. 10 shows a scene from a side-by-side display of a predefined ideal-or-expected motion animation accompanied by a quantitative rating for the motion, a text description of the discrepancies between properties of body part images and the body-model graphics and a color coding reference.

The CPU-Display-Speaker unit 5 in FIG. 1 initiates analysis responses based upon means for matching position-of-interest body part properties of one or more positions-of-interest with the body part image properties as shown in FIG. 8. A quantitative rating 40 in FIG. 10 indicates the quality of the motion performance by comparing the properties of the body part graphics 39 in FIG. 10 representing the ideal-orexpected motion to the properties of the body part images 38 in FIG. 10 of the side-by-side display 38, 39 in FIG. 10. A text description 41 indicates the discrepancies between properties of body part images and the body-model graphics. Color-coding 42 in FIG. 10 of the body part graphics, green for a close match, yellow for a marginally close match and red for a problematic match, is also used to communicate the closeness of the expected-motion to the properties of the body part images 38 in FIG. 10.

The ideal-or-expected body-model animation in FIG. 8 illustrates a complete inter-position-of-interest animation of the four positions-of-interest shown in the example. It transforms body part graphic properties from position-of-interest to position-of-interest so that visual comparisons can be made that reveal closeness of fit between the actual motion of the body in motion and the ideal-or-expected motion.

Figure 11:
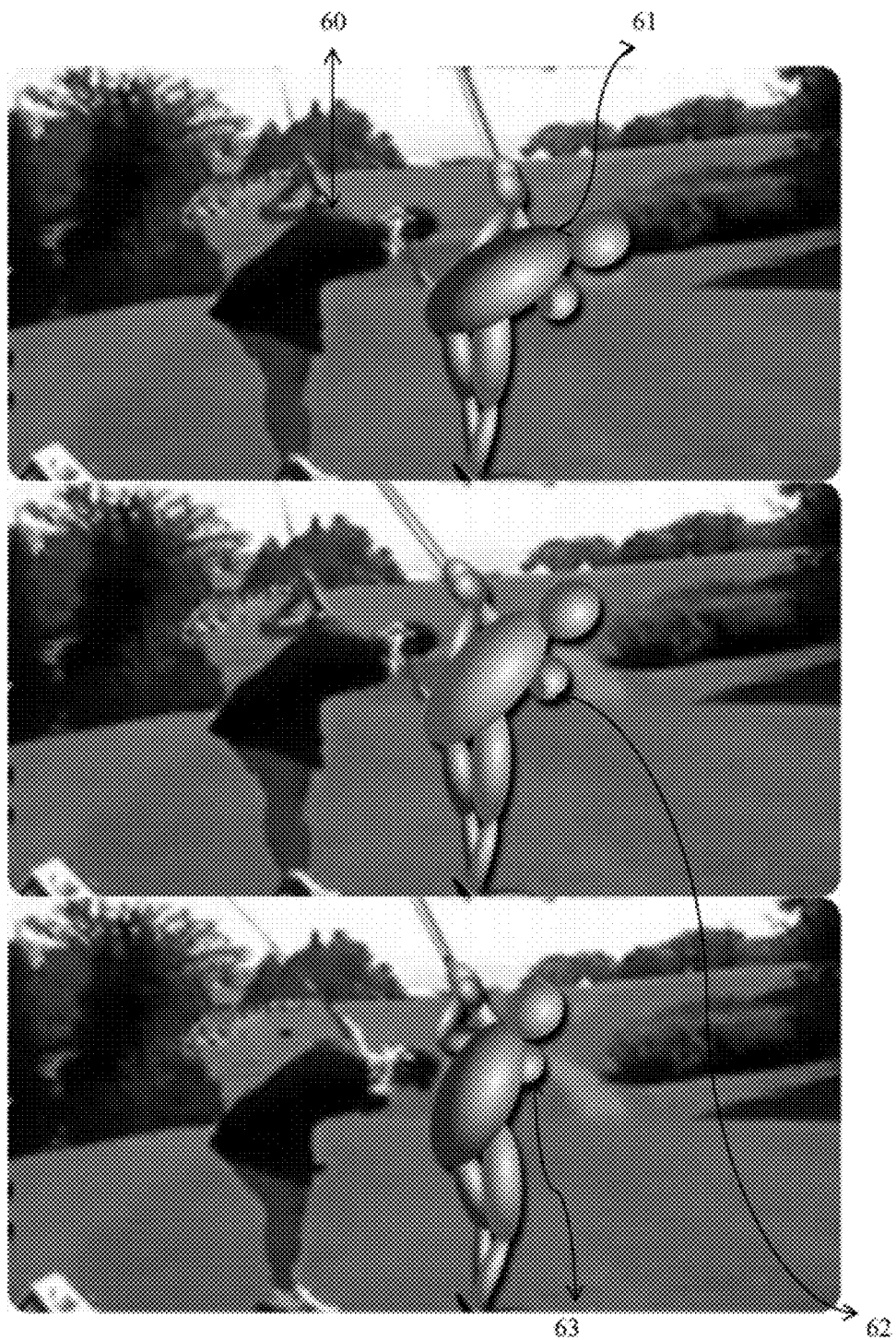
FIG. 11 shows a correction-of-position animation whereby the body part properties of the body-model graphic are animated from the properties of the body part images to the properties of the ideal-or-expected body part graphic.

The correction-of-position animation in FIG. 11 illustrates an intra-position-of-interest animation. This type of body-model animation transforms body part graphic properties from the actual body part image properties 61 in FIG. 11 to the ideal-or-expected properties 63 in FIG. 11 of the same position-of-interest thereby showing a correction-of-position animation.

The upper body parts of the body-model graphic 61 in FIG. 11 represent the body part properties of the body part images 60 in FIG. 11 and are color-coded in red indicating a diversion from the ideal-or-expected motion that is problematic.

As the animation proceeds in 62 in FIG. 11, the upper body part images 60 in FIG. 11 are color-coded in yellow indicating a diversion from the ideal-or-expected motion that is still marginal.

As the correction-of-position animation completes 63 in FIG. 11, the upper body part images 60 in FIG. 11 have turned green indicating no diversion from the ideal-or-expected motion.

What is claimed is:

1. A computer based method of analyzing a body in motion from a video source, comprising:
    displaying at least one image of a plurality of sequential video frames of a subject body in motion;
    determining body properties of the subject body in motion for at least one image of the plurality of sequential video frames,
        wherein said determined body properties include each of a location property, a scale property, and a rotation property for multiple body parts of the subject body in motion;
    displaying at least one image of a smart model animation of an ideal or expected body in motion superimposed on, or beside, the subject body in motion,
        wherein said smart model animation includes adjustable model properties, and
        wherein the adjustable model properties include each of a location property, a scale property and a rotation property for multiple body parts of the smart model animation;
    receiving input from a touch screen or a computer mouse or input of at least one skeletal coordinate from an intelligent video camera that modifies at least one location property, scale property or rotation property of at least one body part of the smart model animation in order to match the at least one modified body part of the smart model animation with at least one body part of the subject body in motion at one or more positions of interest, wherein whenever one of the adjustable model properties of one body part is modified, one or more of the adjustable model properties of at least one other connected body part is correspondingly modified;
    displaying at least one image of the modified smart model animation superimposed on, or beside, the subject body in motion;
    displaying subsequent images of the smart model animation when the subject body in motion is determined to be moving beyond, either forward or backward, a position of interest that matches a position of interest of the smart model animation;
    if subsequent images of the smart model animation contain a level of divergence between the subject body in motion and the smart model animation, displaying a correction of position animation that transforms at least one body part of the smart model animation to match the at least one transformed body part of the smart model animation with at least one body part of the subject body in motion at one or more positions of interest.

2. The method of claim 1, wherein the transform is a result of input from at least one of a touch-sensitive display screen, a computer mouse, a computer keyboard, a game console, a joystick, or an intelligent video camera.

3. The method of claim 1, wherein the the transform is defined according to at least one of a known standard, an external specification, an instructor, an investigator, a therapist, a researcher or a subject.

4. The method of claim 1, wherein the correction of position animation is displayed superimposed over the subject body in motion, beside the subject body in motion or superimposed over a background image without the subject body in motion present.

5. The method of claim 1, wherein the transform begins with body parts of a matched position of interest and end with body parts of a next position of interest.

6. The method of claim 1, further comprising a duration of animation frame count which determines the number of sequential video frames required to complete a position-of-interest animation.

7. The method of claim 1, wherein, during the transform, whenever one body part of the smart model is transformed, at least one other connected body part of the smart model is correspondingly transformed.

8. The method of claim 1, wherein the determining uses image recognition processing.

9. The method of claim 1, further comprising displaying text descriptions, color-coded markings, gradient filled markings, shadows of markings, on and off flashing of markings or-semi-transparent markings.

10. The method of claim 1, further comprising displaying quantitative ratings according to how well the subject body in motion matches the smart model animation.

11. The method of claim 1, further comprising providing audio responses that indicate how well the subject body in motion matches the smart model animation.

12. The method of claim 1, further comprising displaying actual motion transformations of the subject body in motion.

13. The method of claim 1, further comprising displaying ideal or expected motion transformations.

14. The method of claim 1, further comprising receiving video from a recorded video source or a live video source.

15. The method of claim 1, wherein the matching of the at least one modified body part of the smart model animation with the at least one body part of the subject body in motion at one or more positions of interest occurs independently of the direction of said body in motion.

16. The method of claim 1, wherein the smart model animation originates from a body-model template.

17. The method of claim 16, wherein the body-model template is one still image comprising transformable, graphical body part components.

* * * * *